United States Patent [19]

Konrad et al.

[11] Patent Number: 4,713,080
[45] Date of Patent: Dec. 15, 1987

[54] METHOD AND COMPOSITION FOR THE DYEING OF HAIR WITH 2,6-DIAMINO-PYRIDINE DERIVATIVES

[75] Inventors: Eugen Konrad, Darmstadt; Thomas Clausen, Alsbach, both of Fed. Rep. of Germany

[73] Assignee: Wella Aktiengesellschaft, Darmstadt, Fed. Rep. of Germany

[21] Appl. No.: 882,634

[22] Filed: Jul. 7, 1986

[30] Foreign Application Priority Data

Aug. 28, 1985 [DE] Fed. Rep. of Germany ....... 3530732

[51] Int. Cl.$^4$ .............................................. A61K 7/13
[52] U.S. Cl. ......................................... 8/408; 8/409; 8/410; 8/411; 8/412; 546/290; 546/296
[58] Field of Search .................. 8/408, 409, 410, 411, 8/412; 546/290, 296

[56] References Cited

U.S. PATENT DOCUMENTS 3,200,040  8/1965  Lange ..................................... 8/409
4,396,392  8/1983  Konrad et al. .......................... 8/408

FOREIGN PATENT DOCUMENTS 2104922  3/1983  United Kingdom .

OTHER PUBLICATIONS

E. Koenigs, et al, *Chemische Berichte*, 61, p. 1022, (1928).

Primary Examiner—Paul Lieberman
Assistant Examiner—Linda D. Skaling
Attorney, Agent, or Firm—Michael J. Striker

[57] ABSTRACT

A method and composition are disclosed for the oxidative coloration of hair, based upon a developer substance-coupler substance combination, employing as coupler substance at least one 2,6-diamino-pyridine derivative according to Formula I

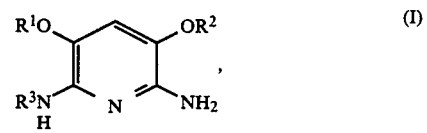

in which $R^1$ and $R^2$ are the same or different and are each $CH_3$ or $C_2H_5$ and $R^3$ is hydrogen, $C_1$-$C_4$-alkyl or $C_1$-$C_4$-hydroxyalkyl, also in the form of the physiologically compatible salts. The coupler substance, preferably 2,6-diamino-3,5-dimethoxy-pyridine, 2,6-diamino-3,5-diethoxy-pyridine and 2-amino-6-(2'-hydroxyethyl)amino-3,5-dimetnoxy-pyridine, should be present in the composition in a concentration from 0.01 to 3.0% by weight, preferably from 0.1 to 2.0% by weight. The coupler substance according to Formula I is storage resistant, well soluble in water and possesses favorable toxicological as well as dermatological characteristics. The coupler substance of Formula I provides, in combination with 1,4-diamino benzene or its derivatives, very intense cold blue tones without red portions, and in combination with 4-aminophenol, strongly lustrous gold-orange tones.

13 Claims, No Drawings

METHOD AND COMPOSITION FOR THE DYEING OF HAIR WITH 2,6-DIAMINO-PYRIDINE DERIVATIVES

BACKGROUND OF THE INVENTION

The subject of this invention is a method and composition for the oxidative coloration (dyeing) of hair, based upon developer substances and coupler substances, in which certain derivatives of 2,6-diamino-pyridine is employed as coupler substance.

Oxidation dyes have acquired a substantial importance for hair coloration. The coloration is produced herewith by means of the reaction of certain developer substances with certain coupler substances in the presence of a suitable oxidation agent.

As developer substances, preferably 2,5-diamino-toluene, 4-amino-phenol and 1,4-diamino-benzene are employed. However, also 2,5-diamino-anisol, 2,5-diamino-benzyl alcohol, 2-(2′-hydroxyethyl)-1,4-diamino-benzene and 4-amino-N-(2′-mesylaminoethyl)-aniline have acquired a certain importance. In determined cases, also tetraamino-pyrimidine can be employed as developer substance.

The preferably employed coupler substances are 1-naphthene, resorcin, 4-chloro-resorcin, m-aminophenol, 5-amino-ocresol and derivatives of m-phenylenediamine, such as e.g. 2,4-diamino-phenetol and 2,4-diamino-anisol. These derivatives, as well as the m-phenylenediamine itself, have acquired herewith a significance as so-called "blue couplers" on account of their capacity to produce blue tones upon the oxidative coupling with 1,4-diamino benzene or 1,4-diamino benzene derivatives.

Numerous particular requirements are placed upon oxidation dyes that are employed for the coloration of human hair. Thus, they must be harmless from both a toxicological and dermatological viewpoint, and make possible the provision of colorations of the desired intensity. It is necessary, moreover, that a broad palette of the most different color nuances can be produced by means of combination of suitable developer and coupler components. In addition, a good fastness to light, permanent waving, acid and rubbing, are required of the obtainable hair colorations. At the very least, such hair colorations must remain stable over a time period of 4 to 6 weeks without being affected by light, chemical agents and rubbing.

The m-phenylenediamine employed for some time as blue coupler in hair coloring compositions, its derivatives 2,4-diamino-toluene and 2,4-diamino-anisol, as well as blue couplers recommended more recently, such as for example 1-hydroxy-3-amino6-chloro-benzene and 2,4-diamino-phenoxyethanol, can not, however, completely satisfactorily fulfill these above mentioned requirements.

SUMMARY OF THE INVENTION

It is therefore an object according to the present invention to make available a hair coloring composition as well as a hair coloring method with which the stated requirements are better fulfilled.

It has now been discovered that compositions for the oxidative coloration of hair, based upon a developer substance-coupler substance combination, thereby characterized in that they contain as coupler substance at least one 2,6-diamino-pyridine derivative of Formula I

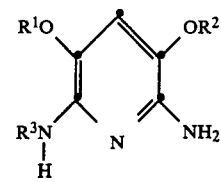

wherein $R^1$ and $R^2$ are the same or different and are each $CH_3$ or $C_2H_5$ and $R^3$ is hydrogen, $C_1$-$C_4$-alkyl or $C_1$-$C_4$-hydroxyalkyl, also in the form of its physiologically compatible salts, meet the stated object to an outstanding extent.

The 2,6-diamino-pyridine derivative of Formula I contained as coupler substance in the hair coloring composition according to the present invention, such as for example 2,6-diamino-3,5-dimethoxy-pyridine, 2,6-diamino-3,5-diethoxy-pyridine and 2-amino-6-(2′-hydroxyethyl)amino-3,5-dimethoxy-pyridine, are well soluble in water. They display, moreover, an excellent storage stability, particularly as components of the here-described hair coloring compositions.

The coupler substances according to the present invention, of which the 2,6-diamino-3,5-dimethoxy-pyridine, 2,6-diamino-3,5-diethoxy-pyridine and 2-amino-6-(2′-hydroxyethyl)amino-3,5-dimethoxy-pyridine are preferred, should be contained in the hair coloring compositions in a concentration from about 0.01 up to 3.0% by weight, preferably from 0.1 up to 2.0% by weight.

The coupler substances of Formula I should be employed in the hair coloring compositions either as free base or in the form of their physiologically compatible salts with inorganic or organic acids, for example, as chloride, sulfate, phosphate, acetate, propionate, lactate or citrate.

Whether or not the advantageous characteristics of the here-described new coupler substances suggest to employ the same as sole coupler, it is obviously also possible to employ the new coupler substances of Formula I together with known coupler substances.

Of the known coupler substances, those coming into consideration as components of the here-described hair coloring compositions are mainly resorcin, 4-chloro-resorcin, 4,6-dichloro-resorcin, 2-methyl-resorcin, 2-amino-4-(2′-hydroxyethyl)amino-anisol, 2,4-diamino-benzyl alcohol, 2,4-diamino-phenylethanol, m-phenylenediamine, 5-amino-2-methyl-phenol, 2,4-diamino-anisol, 2,4-diaminophenoxyethanol, 4-amino-2-hydroxy-phenoxyethanol, 1,5-dihydroxytetralin, 1-naphthene, m-aminophenol, 3-amino-2-methyl-phenol, 4-hydroxy-1,2-methylene-dioxy-benzene, 4-amino-1,2-methylenedioxybenzene, 4-(2′-hydroxyethyl)amino-1,2-methylenedioxy-benzene, 2,4-diamino-phenetol and 4-hydroxy-indol. For the production of certain nuances, also the combination with other heterocyclic couplers, such as for example the 3,5-diamino-2,6-dimethoxy-pyridine or the 3,5-diamino-2,6-di(2′-hydroxyethyloxy)-pyridine described in the DE-OS No. 3 132 885, can be advantageous.

Of the known developer substances suitable as components for the hair coloring composition according to the invention, mention may be made of the following, by way of example: 1,4-diamino-benzene, 2,5-diamino-toluene, 2,5-diamino-anisol, 2,5-diamino-benzyl alcohol, 3-methyl-4-aminophenol, and 4-aminophenol.

The coupler substance of Formula I is generally employed in about molar amounts, relative to the employed developer substances. Although such equimolar employment proves to be expedient, it is still not disadvantageous when the coupler substance is employed in a certain excess or deficiency. It is not, moreover, necessary that the developer component and the coupler component represent, respectively, unitary products. Not only can the developer component represent a mixture of known developer substances, but also the coupler component can represent a mixture of the coupler according to the present invention with other known coupler substances.

The total amount of the developer substance-coupler substance combination contained in the here-described hair coloring compositions should come to about 0.1 to 5.0% by weight, preferably 0.5 to 3.0% by weight.

The hair coloring composition according to the present invention can contain, moreover, additionally other dye components, for example 6-amino-2-methylphenol, 2-amino-5-methylphenol and 2-amino-5-ethoxyphenol, as well as moreover customary direct-drawing-on-the-hair dyes, for example triphenylmethane dyes such as Diamond Fuchsin (C.I. 42 510) and Leather Ruby HF (C.I. 42 520), aromatic nitrodyes, such as 2-nitro-1,4-diaminobenzene, 2-amino-4-nitrophenol and 2-amino-5-nitrophenol, azo-dyes, such as Acid Brown 4 (C.I. 14 805) and Acid Blue 135 (C.I. 13 385), anthraquinone dyes, such as Disperse Red 15 (C.I. 60 710) and Disperse Violet 1 (C.I. 61 100), moreover 1,4,5,8-tetraamino-anthraquinone and 1,4-diamino-anthraquinone.

Obviously, the coupler- and developer-substances, as well as also other dye components, insofar as they are bases, can be employed in the form of the physiologically compatible acid addition salts, such as for example as hydrochloride or sulfate, or—insofar as they possess aromatic OH-groups—in the form of the salts with bases, for example as alkali-phenolate.

In other respects, still further customary cosmetic additives can be provided in the hair coloring compositions according to the present invention, for example antioxidants such as ascorbic acid or sodium sulfite, perfume oils, complex formers, wetting agents, emulsifiers, thickeners, care substances, and the like.

The preparation form can be, for example, a solution, particularly an aqueous or aqueous-alcoholic solution. The particularly preferred form of preparation is, however, a cream, a gel or an emulsion.

Their composition represents a mixture of the dye components with the additives customary for such preparations.

Customary additives in solutions, creams, emulsions or gels are, for example, solvents such as water, lower aliphatic alcohols, for example ethanol, propanol, and isopropanol, as well as multivalent alcohols, such as ethylene glycol, 1,2-propylene glycol and glycerin, moreover wetting agents or emulsifiers from the classes of anionic, cationic, amphoteric or non-ionogenic surface-active substances, such as fatty alcohol sulfate, alkylsulfonate, alkyl benzene sulfonate, alkyltrimethylammonium salt, alkyl betaine, oxethylated fatty alcohol, oxethylated nonylphenol, fatty acid alkanolamide, oxethylated fatty acid ester, moreover thickeners, such as higher fatty alcohols, Bentonite, starch, polyacrylic acid, cellulose derivatives, alginate, vaseline, paraffin oil and fatty acids, as well as moreover care substances, such as lanolin derivatives, cholesterin, pantothenic acid, and betaine. The mentioned components are employed in the amounts customary for such purposes, for example the wetting agent and emulsifiers in concentrations from about 0.5 up to 30% by weight, whereas the thickeners can be contained in the preparations in an amount from about 0.1 up to 25% by weight.

Indeed according to composition, the hair coloring composition according to the present invention can react weakly acid, neutral or alkaline. In particular, it displays a pH-value in the alkaline range between 8.0 and 11.5, whereby the adjustment follows, preferably, with ammonia. One can, however, also employ organic amines, for example monoethanolamine and triethanolamine, or also inorganic bases, such as sodium hydroxide and potassium hydroxide.

For employment for the oxidative coloration of hair, one mixes the above-described hair coloring composition, directly before use, with an oxidation agent, and an amount sufficient for the hair treatment, generally about 60 to 200 g, indeed depending upon the fullness of the hair, of this mixture is applied onto the hair. Coming into consideration as oxidation agent for development of the hair coloration are mainly hydrogen peroxide or its addition compounds with urea, melamine or sodium borate, in the form of 3 to 12% aqueous solutions. If a 6% aqueous solution of hydrogen peroxide is employed as oxidation agent, then the weight ratio between hair coloring composition and oxidation agent amounts from 5:1 to 1:2, preferably however 1:1. Greater amounts of oxidation agent are employed above all with higher dye concentrations in the hair coloring compositions or when simultaneously a stronger bleaching of the hair is intended. One allows the mixture to penetrate into the hair, at a temperature between 15° to 50° C., for a period between about 10 and 45 minutes, preferably about 30 minutes, followed by a rinsing of the hair with water and then drying. If necessary, in connection with this rinsing, the hair is washed with a shampoo and possibly with a weak organic acid, such as for example citric acid or tartaric acid, after-rinsed. Then, the hair is dried.

The manufacture of the compounds of Formula I is described in part in the literature. Thus E. Koenigs, et al. report on the production of 2,6-diamino-3,5-diethoxy-pyridine (Chem. Ber. 61, 1022 (1928)). In contrast, the 2,6-diamino-3,5-dimethoxy-pyridine is new. It can be prepared by means of reduction from the 3,5-dimethoxy-2,6-dinitro-pyridine, analogous to the diethoxy compound. The 3,5-dimethoxy-2,6-dinitro-pyridine is, moreover, analogous to the 2,6-dimethoxy-3,5-dinitro-pyridine, accessible (C. D. Johnson, et al., J. Chem. Soc. (B), 1204 (1967)). The process for the production of the pre-stage 3,5-dimethoxy-pyridine can be improved, in contrast to the literature-known techniques (K. Clarke, et al., J. Chem. Soc. London) 1885 (1960)) and is described in the Examples, infra.

The synthesis of the non-symmetrically substituted 3-ethoxy-5-methoxy-pyridine as pre-stage is possible in hereto analogous manner from 3-bromo-5-methoxy-pyridine (Hertog, et al., Rec. Trav. Chim. Pays-Bas, 74, 1171 (1955)) or from 3-bromo-5-ethoxy-pyridine (Hertog, et al., Rec. Trav. Chim. Pays-Bas, 67, 377 (1948)).

The N-substituted derivatives of 2,6-diamino-3,5-dialkoxy-pyridine corresponding to general Formula I are likewise accessible according to customary synthesis steps described in the literature of preparative organic chemistry. For the purpose, the 3,5-dialkoxy-pyridine compounds are initially mononitrated in the 2-position, and subsequently the nitro-groups are reduced. After the acetylation of the amino-groups, follows the second nitrification in the 5-position. These nitro-groups are likewise reduced, and the obtained amino-groups are mono-alkylated with one of the groups $R^3$ mentioned in the definitions of Formula I. The subsequent saponification of the acetyl groups provides the desired final product. The following reaction schemes should clarify the course of the synthesis.

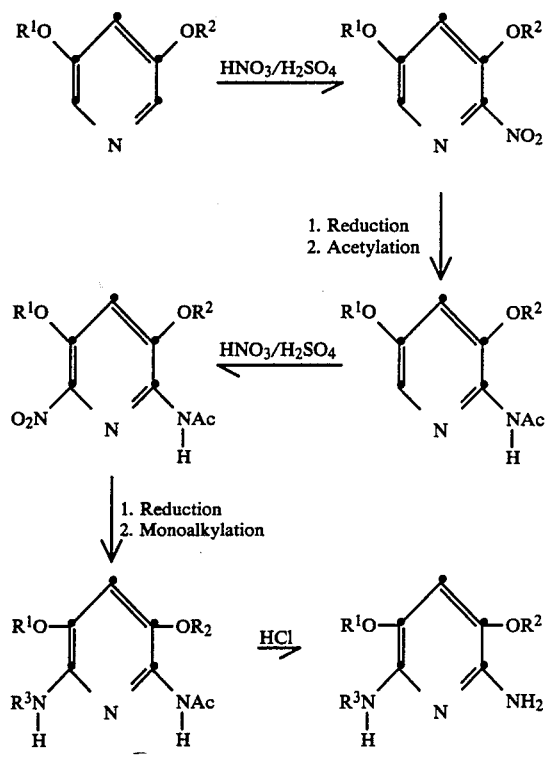

A second possible manner for the synthesis of the compounds of Formula I exists in that a 2,6-dinitro-pyridine substituted in 3,5-position with the groups $R^1$ and $R^2$ is initially partially reduced, subsequently the amino-group is mono-alkylated and then the second nitro-group is likewise reduced. This possibility, which is utilized in the production examples, infra, should be clarified by means of the following reaction scheme:

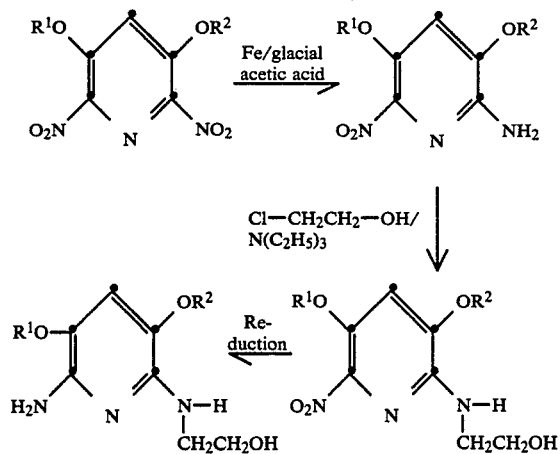

With regard to coloring possibilities, the hair coloring composition according to the present invention offers a broad palette of different color nuances, indeed depending upon type and composition of the color compounds, stretching from blond to brown, ash, matte, gold to blue, and black color tones. Herewith the color tones distinguish by means of their particular color intensity and fastness to light.

The advance obtained through the employment of the 2,6-diamino-pyridine derivatives of Formula I in the here-described hair coloring compositions from the toxicological and dermatological points of view, for example in contrast to the known blue couplers 2,4-diamino-toluene, 2,4-diamino-anisol and m-phenylene-diamine, is of substantial significance. Thus the coupler substances according to the present invention 2,6-diamino-3,5-dimethoxy-pyridine and 2,6-diamino-3,5-diethoxy-pyridine prove, in the Ames Test, to possess no mutagenic activity in *Salmonella typhimurium*, in contrast to 2,4-diamino-toluene or 2,4-diamino-ethyl-benzene.

The preceding set forth pyridine derivatives, as coupler substances in combination with the developer substances 1,4-diamino-benzene and its derivatives, provide very intensive cold blue tones without red overtones.

This facilitates the production of natural color tones, in contrast, for example, to the known coupler component 2-amino-4-(2'-hydroxyethyl)amino-anisol.

Since the blue couplers unconditionally necessary for the production of matte and ash tones promote with the above-mentioned 1,4-diamino-compounds as developer substances, red- or violet-tinged blue tones, the obtaining of ash or matte tones is either impossible or very difficult. In contrast thereto, on account of the advantageous characteristics of the pyridine derivatives of Formula I to produce blue tones without red overtones, it is now possible without problem to permanently dye the hair in ash or matte natural tones, which also remain light stable and do not fade to red as do the nuances produced with m-phenylenediamine.

In contrast to the compounds of Formula II

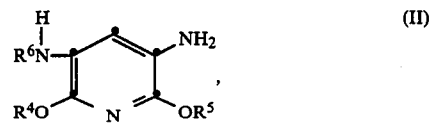

$R^4$, $R^5$=CH$_3$, C$_2$H$_5$, C$_2$H$_4$OH
$R^6$=H, C$_1$-C$_4$-alkyl, C$_1$-C$_4$-hydroxyalkyl
which are described in DE-OS No. 3 132 885, the compounds of Formula I display substantial and surprising advantages. Thus, for example, the compound of Formula I in which $R^1$ and $R^2$ are methyl and $R^3$ is hydrogen, does not couple with itself, and therefore promotes a pure blue without red and green overtones. The compound of Formula II isomeric thereto, in which $R^4$ and $R^5$ are methyl and $R^6$ is hydrogen, indeed colors in a blue-black tone without red overtones, however with a green overtone. This can have a disturbing effect upon the production of ash tones. The cold, very pure blue color, which is obtained upon coloration of the compounds of Formula I with customary developer components, considerably facilitates the production of ash tones. A further advantage is the slight sensitivity of the 2,6-diamino-pyridine compounds with respect to air oxygen. This is advantageous during the formulation of dye preparations.

The above mentioned results were not to be expected. Likewise, one cannot generally presume that isomers color equally well. An example of this would be the likewise isomeric amino-hydroxy-pyridine compounds III and IV.

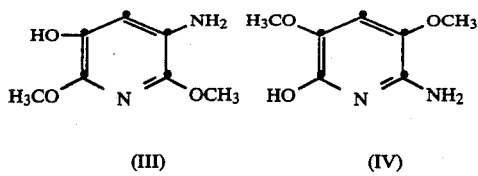

(III)  (IV)

Whereas the compound III, which is described in DE-OS No. 3 442 128, displays very good color characteristics as a red coupler, the compound IV, isomeric thereto, is not useful on account of its too slight depth of color.

A further advantage of the 2,6-diamino-pyridine derivatives contained in the hair coloring compositions according to the present invention is the broad spectrum of produceable color tones. They can, for example, in combination with 4-amino-phenol as developer substance, produce strongly luminous, mod goldorange tones, for the production of which mixtures of different couplers previously had to be employed.

Finally, it is also possible with the aid of the hair coloring compositions according to the present invention to dye grayed, chemically uninjured hair without problem and with very good covering power.

The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

Production Examples

Example 1

Production of 2,6-diamino-3,5-dimethoxy-pyridine-dihydrochloride (a) 3,5-dimethoxy-pyridine 50 g of 3,5-dichloro-pyridine are dissolved in 250 ml dimethylsulfoxide. 15 g sodium methylate are added to this solution under stirring. It is stirred under exclusion of moisture at 60°–80° C. 15 g sodium methylate are further added after each of 8 and 16 hours. After a total of 72 hours' stirring, the reaction mixture is reacted with a little water and shaked out with diethylether. The ether phase, after drying, is distilled in a vacuum, resulting in 24 g (51% of theoretical amount) of 3,5-dimethoxy-pyridine in the boiling range 90°–120° C. at $1.6 \cdot 10^3$ Pa. The product is polluted with a small amount of 3-chloro-5-methoxypyridine. It can, however, be employed directly in the next stage for nitrification, since the chloro-compound is not dinitrified and therefore can easily be removed upon crystallization of the 3,5-dimethoxy-2,6-dinitro-pyridine.

(b) 2,6-diamino-3,5-dimethoxy-pyridine-dihydrochloride

The nitrification of the 3,5-dimethoxy-pyridine, as well as the subsequent reduction of the 3,5-dimethoxy-2,6-dinitro-pyridine into 2,6-diamino-3,5-dimethoxy-pyridine, are performed analogous to the description by E. Koenigs, et al., Chem. Ber. 61, 1022 (1928). In the organic phase obtained after the shaking out with diethylether, HCl gas is introduced, and the precipitating sediment is evacuated in a vacuum. The 2,6-diamino-3,5-dimethoxypyridine precipitating as dihydrochloride melts at 160° C. with decomposition.

$^1$H-NMR-spectrum (dimethylsulfoxide-$d_6$, $\delta$ in ppm: 7.6 (s, broad NH$_2$m exchangeable with D$_2$O); 7.49 (s, 4-H); 3.80 (s, 2 times OCH$_3$).

For this and the following NMR-spectra, the following abbreviations are employed: s=singlet, m=multiplet.

Example 2

Production of 2-amino-6-(2'-hydroxyethyl) amino-3,5-dimethoxy-pyridine-dihydrochloride (a) 2-amino-3,5-dimethoxy-6-nitro-pyridine The 3,5-dimethoxy-2,6-dinitro-pyridine produced in Example 1, stage (b), is treated analogous to the reduction of the 1,2-dimethoxy-4,5-dinitro-benzene with iron in glacial acetic acid according to D. A. Wulfman, et al., Synthesis, 924 (1978). Therewith, under nitrogen, a solution of 200 mg (0.87 mmol) of the dinitro-compound is produced in 5 ml glacial acetic acid and heated to boiling. 145 mg (2.60 mmol) of iron powder are then added thereto. After ten minutes' cooking under reflux, the reaction mixture is cast onto an ice-water mixture and the depositing reaction product is separated by means of filtration. Chromatography in silica gel with a mixture of methylene chloride and methanol in a ratio of 9:1 provides the pure 2-amino-3,5-dimethoxy-6-nitro-pyridine with a melting point of 195° C.

(b) 2-(2'-hydroxyethyl)amino-3,5-dimethoxy-6-nitro-pyridine 500 mg (2.5 mmol) of 2-amino-3,5-dimethoxy-6-nitro-pyridine are dissolved in 2 ml ethylene chloride and the solution is heated to 30° C. Under stirring, 1 ml triethylamine is added and then heated to 100° C. for 10 hours. Subsequently, the reaction mixture is cast onto ice and the precipitating reaction product is separated by means of filtration. The purification follows by means of chromatography in silica gel with methylene chloride and ethyl acetate in a ratio of 1:1 as flow agent. One obtains the 2-(2'-hydroxyethyl)amino-3,5-dimethoxy-6-nitro-pyridine in the form of orange crystals with a melting point of 131° C.

$^1$H-NMR-spectrum (dimethylsulfoxide-$d_6$, $\delta$ in ppm): 7.20 (s, 4-H); 6.17 (broad, NH, exchangeable with D$_2$O); 4.55 (broad, OH, exchangeable with D$_2$O); 4.02 (s, 5-OCH$_3$); 3.92 (s, 3-OCH$_3$); 3.60–3.15 (m, —OC$\underline{H}_2$C-$\underline{H}_2$OH).

(c) 2-amino-6-(2'-hydroxyethyl)amino-3,5-dimethoxy-pyridine-dihydrochloride 100 mg of the 2-(2'-hydroxyethyl)amino-3,5-dimethoxy-6-nitro-pyridine are hydrated in 10 ml methanol on platinum at normal pressure and room temperature. After conclusion of the hydrogen withdrawal, the catalyst is filtered off, the filtrate is adjusted weakly acid with hydrochloric acid, and the solvent is distilled off in a vacuum. The 2-amino-6-(2'-hydroxyethyl) amino-3,5-dimethoxy-pyridine-dihydrochloride precipitating as a finely crystalline, gray residue, is employed directly for the coloration tests according to Example 5, infra.

Examples for Hair Coloring Compositions

Example 3

Hair Coloring Composition in Gel Form

| | |
|---|---|
| 0.75 g | 2,6-diamino-3,5-dimethoxy-pyridine-dihydrochloride |
| 0.70 g | 2,5-diamino-toluene sulfate |
| 0.30 g | ascorbic acid |
| 1.00 g | hydroxyethyl cellulose, highly viscous |
| 5.00 g | lauryl alcohol-diglycolether-sulfate, sodium salt (28% aqueous solution) |
| 10.00 g | ammonia, 22% |
| 82.25 g | water |
| 100.00 g | |

50 g of the above hair coloring composition are mixed, shortly before use, with 50 ml hydrogen peroxide solution (6%), and the mixture is subsequently applied onto white human hair. After a penetration period of 30 minutes at about 40° C., the hair is rinsed with water and then dried. The hair is colored deep blue.

Example 4

Hair Coloring Composition in Gel Form

| | |
|---|---|
| 0.50 g | 2,6-diamino-3,5-diethoxy-pyridine-dihydrochloride |
| 0.50 g | 2,5-diamino-toluene sulfate |
| 0.30 g | ascorbic acid |
| 1.00 g | hydroxyethyl cellulose, highly viscous |
| 5.00 g | lauryl alcohol-diglycolether-sulfate, sodium salt (28% aqueous solution) |
| 10.00 g | ammonia, 22% |
| 82.70 g | water |
| 100.00 g | |

50 g of the above hair coloring composition are mixed, briefly before use, with 50 ml hydrogen peroxide solution (6%) and the mixture is subsequently applied onto blond human hair. After a working-in period of 30 minutes, at a temperature of 40° C., the hair is rinsed with water and then dried. The hair is colored in an intensive blue tone.

Example 5

Hair Coloring Composition in Gel Form

| | |
|---|---|
| 0.80 g | 2-amino-6-(2'-hydroxyethyl)amino-3,5-dimethoxy-pyridine-dihydrochloride |
| 0.30 g | 1,4-diamino-benzene |
| 0.25 g | resorcin |
| 0.30 g | ascorbic acid |
| 15.00 g | oleic acid |
| 7.00 g | isopropanol |
| 10.00 g | ammonia, 22% |
| 67.70 g | water |
| 100.00 g | |

Briefly before use, one mixes 50 g of this hair coloring composition with 50 ml hydrogen peroxide solution (6%) and allows the mixture to penetrate into white human hair for a period of 30 minutes at a temperature of 40° C. Thereafter, the hair is rinsed with water and then dried. The hair has obtained a natural looking medium ash blond coloration.

Example 6

Hair Coloring Composition in Cream Form

| | |
|---|---|
| 0.60 g | 2,6-diamino-3,5-dimethoxy-pyridine-dihydrochloride |
| 0.30 g | 4-amino-phenol |
| 0.30 g | sodium sulfite, water-free |
| 3.50 g | lauryl alcohol-diglycolether-sulfate, sodium salt (28% aqueous solution) |
| 15.00 g | cetyl alcohol |
| 3.00 g | ammonia, 22% |
| 77.30 g | water |
| 100.00 g | |

50 g of this hair coloring composition are mixed with 50 ml hydrogen peroxide solution (6%) briefly before use, and the mixture is subsequently applied onto white human hair. After a penetration period of 30 minutes at a temperature of 40° C., the hair is rinsed initially with water and then with a dilute citric acid solution, and finally dried. The hair is colored in a mod gold-orange color tone.

Example 7

Aqueous Hair Coloring Composition

| | |
|---|---|
| 1.50 g | 2,6-diamino-3,5-dimethoxy-pyridine-dihydrochloride |
| 1.80 g | resorcin |
| 0.30 g | m-aminophenol |
| 5.00 g | 2,5-diamino-toluene-sulfate |
| 6.00 g | isopropanol |
| 0.10 g | sodium sulfite, water-free |
| 7.00 g | ammonia, 22% |
| 78.30 g | water |
| 100.00 g | |

50 g of this hair coloring composition are mixed with 50 ml of hydrogen peroxide solution (6%) briefly before use, and the mixture is then applied onto white human hair. after a penetration period of 30 minutes at a temperature of 40° C., the hair is rinsed with water first, and then with dilute citric acid solution, and then dried. The hair is colored a deep blue-black.

All percentages set forth in this specification, insofar as it is not stated otherwise, represent percent by weight.

It will be understood that each of the elements described above, or two or more together, may also find a useful application in other types of hair coloring compositions differing from the types described above.

While the invention has been illustrated and described as embodied in a method and composition for the dyeing of hair with 2,6-diamino-pyridine derivatives, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Composition for the oxidative coloration of hair, based upon 1.0 to 5.0 by weight of a developer substance-coupler substance combination, comprising an effective amount of a developer substance and as a coupler substance 0.01 to 3.0% by weight of at least one 2,6-diaminopyridine derivative according to Formula I:

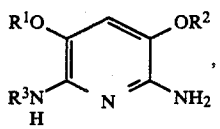

wherein $R^1$ and $R^2$ are the same or different and are each $CH_3$ or $C_2H_5$ and $R^3$ is hydrogen, $C_1$–$C_4$-alkyl or $C_1$–$C_4$-hydroxylalkyl, or a physiologically compatible salt thereof.

2. The composition according to claim 1, containing said coupler substance of Formula I in an amount between about 0.1 and 2.0% by weight.

3. The composition according to claim 1, wherein said coupler substance of Formula I is selected from 2,6-diamino-3,5-dimethoxy-pyridine, 2,6-diamino-3,5-diethoxy-pyridine, 2-amino6-(2'-hydroxyethyl)amino-3,5-dimethoxy-pyridine or the physiologically compatible salts thereof.

4. The composition according to claim 1, further comprising a known coupler substance selected from the group consisting of resorcin, 4-chloro-resorcin, 2-methyl-resorcin, 4,6-dichloro-resorcin, 2,4-diaminobenzyl alcohol, 2-amino-4-(2'-hydroxyethyl)amino-anisol, 2,4-diamino-phenylethanol, 2,4-diamino-phenoxyethanol, 2,4-diamino-anisol, 2,4-diamino-phenetol, 3,5-diamino-2,6-dimethoxy-pyridine, 3,5-diamino-2,6-di(2'-hydroxyethyloxy)pyridine, 1,5-dihydroxy-tetralin, m-aminophenol, 3-amino-2-methylphenol, 5-amino-2-methyl-phenol, 4-hydroxy-1,2-methylenedioxybenzene and 4-(2'-hydroxyethyl)amino-1,2-methylenedioxy-benzene.

5. The composition according to claim 1, wherein said developer substance is selected from the group consisting of 1,4-diamino-benzene, 2,5-diamino-toluene, 2,5-diamino-anisol, 2,5-diamino-benzyl alcohol, 3-methyl-4-amino-phenol and 4-amino-phenol.

6. The composition according to claim 1, wherein the total amount of the coupler substance-developer substance combination is between about 0.1 and 5.0% by weight.

7. The composition according to claim 6, wherein said total amount is between about 0.5 and 3.0% by weight.

8. The composition according to claim 1, further comprising a color component selected from the group consisting of 6-amino-2-methyl-phenol, 2-amino-5-methyl-phenol, 2-amino-5-ethoxy-phenol, Diamond Fuchsin (C.I. 42 510), Leather Ruby HF (C.I. 42 520), 2-nitro-1,4-diamino-benzene, 2-amino-4-nitrophenol, 2-amino-5-nitro-phenol, Acid Brown 4 (C.I. 14 805), Acid Blue 135 (C.I. 13 385), Disperse Red 15 (C.I. 60 710), Disperse Violet 1 (C.I. 61 100), 1,4,5,8-tetraaminoanthraquinone and 1,4-diamino-anthraquinone.

9. The composition according to claim 1, further comprising an antioxidant.

10. The composition according to claim 10, wherein said antioxidant is ascorbic acid or sodium sulfite.

11. The composition according to claim 1, displaying a pH-value from 8.0 to 11.5.

12. Method for the oxidative coloration of hair, comprising mixing the hair coloring composition according to claim 1 directly before use with an oxidation agent, applying an amount sufficient for the treatment of hair of said mixture onto the hair, leaving said mixture on said hair for a penetration period between about 10 and 45 minutes at a temperature between about 15° and 50° C., rinsing said hair with water, with or without washing said hair with a shampoo, after-rinsing said hair with an acid after-treatment agent and then drying said hair.

13. The method according to claim 12, wherein said oxidation agent is hydrogen peroxide or its addition compounds with urea, melamine or sodium borate.

* * * * *